United States Patent [19]

Langerbeins et al.

[11] Patent Number: 4,774,349

[45] Date of Patent: Sep. 27, 1988

[54] METHOD OF PREPARING N-METHYLPHOSPHONIC ACID DIESTERS OF ACRYLIC AND METHACRYLIC ACID AMINES FROM METHYLOL

[75] Inventors: Klaus Langerbeins, Langen; Werner Ude, Darmstadt, both of Fed. Rep. of Germany

[73] Assignee: Rohm GmbH Chemische Fabrik, Darmstadt, Fed. Rep. of Germany

[21] Appl. No.: 918,051

[22] Filed: Oct. 14, 1986

[30] Foreign Application Priority Data

Nov. 13, 1985 [DE] Fed. Rep. of Germany ....... 3540217

[51] Int. Cl.$^4$ .............................................. C07F 9/40
[52] U.S. Cl. ...................................... 558/122; 558/83
[58] Field of Search ................................. 558/122, 83

[56] References Cited

U.S. PATENT DOCUMENTS 3,763,108 10/1973 Chang et al. ......................... 558/170
3,884,628 5/1975 Duffy et al. ......................... 8/116 P

FOREIGN PATENT DOCUMENTS 2215434 3/1972 Fed. Rep. of Germany .
2217746 4/1972 Fed. Rep. of Germany .
2538282 8/1975 Fed. Rep. of Germany .
1380675 4/1973 United Kingdom .
619486 8/1978 U.S.S.R. .............................. 558/122

OTHER PUBLICATIONS

Tetrahedron Letters, Band 22, Nr. 34, 1981, Seiten 3249–3252, Pergamon Press Ltd., GB; T. Shono et al: "A New Carbon–Phosphorous Bond Forming Reaction and Synthesis of Aminoalkylphosphonic Acid Derivatives", Insgesamt.

*Primary Examiner*—Anton H. Sutto
*Attorney, Agent, or Firm*—Oblon, Fisher, Spivak, McClelland & Maier

[57] ABSTRACT

A process for the preparation of (meth)acrylamidomethylphosphonic acid diesters of formula I:

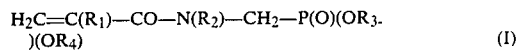

$$H_2C=C(R_1)-CO-N(R_2)-CH_2-P(O)(OR_3)(OR_4) \quad (I)$$

is disclosed. In the above formula, $R_1$ is a hydrogen atom or methyl group. $R_2$ is a hydrogen atom, a $C_1$-$C_4$ alkyl group (which can be substituted) or a $C_3$-$C_4$ alkenyl group. $R_3$ and $R_4$ are each independently a phenyl group, or an alkyl group (which can be substituted) having 1–4 C atoms. Or $R_3$ and $R_4$ together form an alkylene group which forms a 5- or 7-membered ring with the oxygen atoms and the phosphorus atoms.

The process is based on reacting a N-methylol derivative of (meth)acrylamide with a phosphorous acid triester, in which a N-methylol ether of a (meth)acrylamide is used. The reaction can be advantageously catalyzed by Lewis acids.

22 Claims, No Drawings

METHOD OF PREPARING N-METHYLPHOSPHONIC ACID DIESTERS OF ACRYLIC AND METHACRYLIC ACID AMINES FROM METHYLOL

BACKGROUND OF THE INVENTION

1. Field of the Invention

The invention relates to a method of preparing polymerizable phosphonic acid diesters by reacting N-hydroxymethyl derivatives of (meth)acrylic acid amides with tertiary phosphites (i.e., phosphorous acid triesters).

2. Discussion of the Background

A number of different processes have been described previously for preparing compounds of general formula I:

$$H_2C=C(R_1)-CO-N(R_2)-CH_2-P(O)(OR_3)(OR_4) \quad (I)$$

where
$R_1$ is a hydrogen atom or a methyl group;
$R_2$ is a hydrogen atom or a $C_1-C_4$ alkyl group, which can optionally be substituted, or a $C_3-C_4$ alkenyl group; and
$R_3$ and $R_4$ are identical or different groups such as phenyl, or $C_{1-4}$ alkyl groups (possibly substituted), or alkylene groups which form 5- to 7-membered rings with the oxygen atoms and the phosphorus atom.

The known methods for preparing these compounds start from (meth)acrylic acid amide derivatives of formula II:

$$H_2C=C(R_1)-CO-N(R_2)-CH_2-X \quad (II)$$

where $R_1$ and $R_2$ have the meanings given supra, and X is a dimethylamino group, a diethylamino group, an acetoxy group, a propanoyloxy group, a halogen atom, or a hydroxyl group. The compounds of formula II are then reacted with tertiary phosphites (phosphorus acid triesters), particularly aliphatic phosphorous acid triesters of formula III:

$$P(OR_3)(OR_4)(OR_5) \quad (III)$$

where $R_3$, $R_4$ and $R_5$ are identical or different groups, such as phenyl or $C_{1-4}$ alkyl groups, or $R_3$ and $R_4$ are alkylene groups which form 5- to 7-membered rings with the oxygen atoms and the phosphorus atom.

Thus, German OS No. 22 15 434 (which corresponds to U.S. Pat. No. 3,884,618) describes the reaction of phosphorous acid triesters with compounds of formula II where X is a OH group, at temperatures of about 100°–200° C. to produce a raw product. German OS No. 22 17 746 (which corresponds to U.S. Pat. No. 1,380,675) describes reactions of (meth)acrylamide derivatives of formula II (where X represents the various moieties indicated supra) with phosphorous acid triesters of formula III.

The polymerizable phosphonic acid esters of formula I are relatively high boiling substances. Thus, in German OS No. 22 17 746, 0,0-dimethyl N-methacrylamido-methylphosphonate is obtained as a liquid with a boiling point of 170° to 180° C. (at 1.2 to 1.5 Torr) in a yield of 76% of theoretical, from N-(acetoxymethyl)-methacrylamide. A corresponding undistilled raw product obtained from N-(hydroxymethyl)-methacrylamide should be comprised of this compound in amounts of up to 78% by wt. according to gc analysis.

Attempts to prepare (meth)acrylamidomethylphosphonates in high yields and high purities have been unsuccessful. Reactions carried out under the known reaction conditions produce relatively large amounts of methylenebisamides of (meth)acrylic acid from N-hydroxymethyl derivatives of (meth)acrylic acid amide, etc. If these bisamides are not removed by purification processes which are costly and lead to substantial losses of materials, they act as spurious crosslinking agents in the manufacture of polymers. References to the inadequate purity of the reaction products obtained can be found in German OS No. 25 38 282, where it is stated that the reaction products of reactions according to e.g., German OS No. 22 17 746, are mixtures of monomeric and oligomeric phosphonates.

As indicated in 1962 *Makromolekulare Chem.* 57:27, starting compounds (II) in which X is an acyloxy (e.g. acetoxy or propanoyloxy) group (as described in German OS No. 22 17 746) may be prepared by esterification of the corresponding methylol compounds by the appropriate carboxylic acid anhydrides. These anhydrides are however relatively costly materials, and the yields achieved, e.g., a 67% of theoretical yield of acetoxymethyl-methacrylamide, are relatively low.

These substances are required for the manufacture of industrially important polymers. There is therefore a strongly felt need for an improved method to obtain these polymerizable phosphonic acid esters and derivatives produced from these phosphonic acid esters in increased yield and purity (e.g. by substantial suppression of side reactions). Such a method should ideally produce raw products which can be used directly.

SUMMARY OF THE INVENTION

Accordingly, it is an object of this invention to provide a novel process for the production of polymerizable phosphonic acid esters and their derivatives.

It is another object of this invention to provide a process which produces polymerizable phosphonic acid esters method esters and their derivatives in high yields.

It is another object of this invention to provide a process for producing polymerizable phosphonic acid esters and their derivatives in high purity.

It is another object of this invention to provide a process for producing polymerizable phosphonic acid esters and their derivatives in which the raw reaction product can be used directly.

The present invention relates to the inventors' surprisingly discovery of a process which satisfies all of the objects of this invention outlined above and other objects which will become obvious from the description of the invention given herein below. The process of the present invention provides (meth)acrylamidomethylphosphonic acid diesters of formula I:

$$H_2C=C(R_1)-CO-NR_2-CH_2-P(O)(OR_3)(OR_4) \quad (I)$$

In formula I, $R_1$ is a hydrogen atom or a methyl group. $R_2$ is a hydrogen atom, an unsubstituted $C_1-C_4$ alkyl group, a substituted $C_1-C_4$ alkyl group, or a $C_3-C_4$ alkenyl group. $R_3$ and $R_4$ are each independently a phenyl group, an unsubstituted $C_1-C_4$ alkyl group, a substituted $C_1-C_4$ alkyl group, or $R_3$ and $R_4$ together form an alkylene group forming 5- to 7-membered ring with the oxygen atoms and the phosphorous atom.

The process of the present invention comprises reacting a methylamide derivative of (meth)acrylic acid of formula II $$H_2C=C(R_1)-CO-NR_2-CH_2-X \qquad (II)$$

with a phosphorous acid triester of formula III $$P(OR_3)(OR_4)(OR_5) \qquad (III).$$

In the compounds of formula II, $R_1$ and $R_2$ have the definitions given for formula I. X is a $C_1$-$C_{10}$ alkoxy group or a $C_1$-$C_{10}$ alkenyloxy group. In the compounds of formula III, $R_3$, $R_4$, and $R_5$ are each independently a phenyl group, an unsubstituted $C_1$-$C_4$ alkyl group, a substituted $C_1$-$C_4$ alkyl group. Or $R_3$ and $R_4$ together form an alkylene group forming a 5- to 7-membered ring with the oxygen atom and the phosphorous atom.

DETAILED DESCRIPTION OF THE PREFERRED EMBODIMENTS

Thus the invention relates to a method of preparing polymerizable phosphonic acid diesters by reacting N-hydroxymethyl derivatives of (meth)acrylic acid amides with tertiary phosphites (i.e., phosphorous acid triesters). These monomers, or their acids or salts prepared by hydrolysis, yield polymers (e.g., plastics, textile additives, or textile auxiliary agents) which have improved properties, e.g. improved fire retardancy.

The process of the present invention relates to the preparation of (meth)acrylamidomethylphosphonic acid diesters of formula I by reacting a methacrylic acid amide derivatives of formula II where X is a $C_1$-$C_{10}$ alkoxy group or a $C_2$-$C_{10}$ alkenoxy group) with phosphorous acid triesters, particularly those of formula III. Surprisingly, when one uses readily available and stabile N-methyl alkyl or N-methyl alkenyl ethers of (meth)acrylamide (which are disclosed in *Makromolekulare Chem.* loc. cit.) in the reaction with phosphorous acid triesters, one obtains substantially higher yields of the corresponding polymerizable phosphonic acid diesters than when one uses the known starting substances of the type —$CH_2$—X defined supra.

It has also been discovered that the reactions of the N-methyl alk(en)yl ethers of the unsaturated amides with the phosphorous acid triesters are advantageously carried out in the presence of Lewis acids. This accelerates the desired reactions and surprisingly suppresses side reactions.

The present process is carried out according to the following reaction scheme:

$$H_2C=C(R_1)-CO-N(R_2)-CH_2-O-Alk+\\P(OR_3)(OR_4)(OR_5)\rightarrow H_2C=C(R_1)-CO-N(R_2)-CH_2-P(O)(OR_3)(OR_4)+Alk-O-R_5$$

$R_1$, $R_2$, $R_3$, $R_4$ and $R_5$ in the above illustration have the meanings given supra. Alk is a $C_{1-10}$ alkyl or $C_{2-10}$ alkenyl group, which each may be straight, branched, cyclic or aralphatic. The reaction can be carried out neat or in the process of an inert diluent or solvent, in either case, at 30°–180° C., preferably 60°–130° C. The reaction can be preferably run in the presence of at least one catalytically active metal compound. The reactants can be provided in an about stoichiometric ratio. Preferably, an excess of the phosphorus acid triester can be used. The ether formed in the reaction may be distilled-off during the reaction.

Examples of (meth)acrylamidomethyl ethers which can be used for preparing the polymerizable amido phosphonic acid esters are: N-(methoxymethyl)-(meth)acrylamide, N-(ethoxymethyl)-methacrylamide, N-(isobutoxymethyl)-(meth)acrylamide, N-(methoxymethyl)-N-methyl-methacrylamide, N-(isobutoxymethyl)-N-methyl-methacrylamide, N-(ethoxymethyl)-N-ethyl-acrylamide, N-(allyloxymethyl)-methacrylamide, and N-(cyclohexyloxymethyl)-methacrylamide. N-(methoxymethyl)-(meth)acrylamide, N-(ethoxymethyl)-(meth)acrylamide, and N-(isobutoxymethyl)-(meth)acrylamide, all of which can be prepared industrially in high purities, are preferred.

In addition to phosphorous acid triphenyl esters, compounds which are particularly good candidates for the phosphorous acid triester reactants are aliphatic phosphorous acid triesters. The following phosphorous acid triesters might be mentioned, as examples: trimethyl ester, triethyl ester, triisopropyl ester, tri-n-butyl ester, tri-(2-chloroethyl)ester, tri-(2-bromomethyl)ester, 2-methoxy-1,3-dioxaphospholane, and 2-ethoxy-4-methyl-1,3-dioxaphospholane.

The above-mentioned phosphorous acid triesters are liquids. Even the triphenyl ester, which has a melting point of 25° C., is a liquid at the reaction temperatures. The phosphorous acid triesters are added to the unsaturated amidomethyl ether components in at least equimolar amounts. Advantageously the phosphorous acid triesters can be added in a two-fold to an eight-fold excess.

The triesters can serve as the reaction medium. After the reaction has been completed, the excess phosphorous acid triester is distilled-off, optionally at reduced pressure. If the reaction is carried out with an inert solvent or diluent, the excess phosphorous acid triester may be kept relatively small, as a reactant, and in fact the reactants may even be provided in a 1:1 molar ratio. Suitable reaction media include, e.g., dichloromethane, 1,2-dichloroethane, tetrachloroethane, chlorofluoro hydrocarbons, or even nitrobenzene.

In the reaction, one mole of dialkyl or phenylalkyl ether is formed (depending on the starting components) for each mole of reaction product formed. This ether may be distilled-off during the reaction, along with excess phosphorous acid triester and solvent. After the reaction, all volatile substances, such as excess phosphorous acid triester, ethers, and solvent (if present) are distilled-off at reduced pressure. The remaining product can then be used without additional purification.

It has also been discovered, in connection with this invention, that the reaction can be accelerated and the yield improved by using Lewis acids. Catalysts having a Lewis acid character (see "Roempps Chemie Lexikon" (a chemical dictionary), 8th Ed., p. 2360) which can be used in the present invention include the following:

Inorganic metal compounds known to be used as Friedel-Crafts catalysts. These are generally halides, e.g. $AlCl_3$, $AlBr_3$, $BF_3$, $ZrCl_4$, $ZnCl_2$, $TiCl_4$, $BeCl_2$, $BiCl_3$, $AsF_3$, $FeCl_3$, $SbCl_5$, $CuCl_2$, and $SnCl_4$ (see also "Ullmanns" Encyclopaedie der technischen Chemie", 4th Ed., Vol. 7, p. 101, and Vol. 14, p. 675).

Compounds of the metals titanium, zirconium, hafnium, tin, zinc, aluminum, and vanadium, having organic ligands (such as alkoxy-, aryloxy-, acyloxy-, or even alkyl- or aryl-ligands, where the alkyl, acyl, or aryl groups have 1 to 10 C atoms). Examples are tetraisopropyl titanate, tetra-n-butyl titanate, dibutyltin oxide, and zircon (IV) alcoholates (especially with propanol and butanol). The acyloxy derivatives of the metals may be acetates, e.g. zinc acetate, or (meth)acrylates. Another useful class of catalysts with organic groups are metal acetylacetonates, e.g. zirconium or titanium acetylacetonate. These Lewis acids are frequently used as esterification catalysts in synthetic chemistry (see "Ullmanns Encyclopaedie der technischen Chemie", 4th Ed., Vol. 11, p. 91, and the publications "Titanansaeureester" ("Titanium acid esters") and "Zwischenprodukte and Katalysatoren" ("intermediate products and catalysts"), of the firm Dynamit Nobel Chemikalien.

Combinations of two or more catalysts of the groups mentioned may also be advantageously used, e.g.: $AlCl_3$ and ethyl zircon(IV)ate; or Ti(IV) compounds with dialkyltin oxides (e.g. tetraisopropyl titanate and dibutyltin oxide). These may be employed in various mole ratios.

Catalytic amounts of metal compounds are used in the present invention for catalyzing the reaction of (meth)acrylamidomethyl alkyl ethers and phosphorous acid triesters, e.g. 0.01 to 10 mol.%, preferably 0.1 to 5 mol.%, based on the amount of phosphonic acid ester to be produced.

In order to avoid polymerization losses, it is advantageous to carry out the reaction and subsequent processing of the reaction mixture in the presence of polymerization inhibitors, e.g. hydroquinone monomethyl ether.

Other features of the invention will become apparent in the course of the following description of exemplary embodiments which are given for illustration of the invention and are not intended to be limiting thereof.

EXAMPLE 1

10 mol N-(methyoxymethyl)-methacrylamide (98%), 15 mol phosphorous acid trimethyl ester, and 1 g hydroquinone monomethyl ether were heated to 110° C. in a three-neck round-bottom flask equipped with a reflux condenser, a compressed air inlet, a thermometer, a distillation head, and a mechanical stirrer. After the addition of 27 ml isopropoyl titanate, the reaction mixture was maintained at 110° C. for 16 hr under reflux. The excess phosphorous acid trimethyl ester was distilled-off under vacuum (oil pump). The remaining 1819 g methacrylamidomethylphosphonic acid dimethyl ester had a purity of 90%, based on $^1H$ and $^{31}P$ nmr spectra, corresponding to a yield of 81% of theoretical.

EXAMPLE 2

0.33 mol N-(methoxymethyl)-methacrylamide (98%), 0.5 mol phosphorous acid trimethyl ester, and 0.1 g hydroquinone monomethyl ether were heated to 110° C. in a three-neck round-bottom flask equipped with a reflux condenser, a compressed air inlet, a thermometer, a distillation head, and a mechanical stirrer. After the addition of 1 g dibutylin oxide, the reaction mixture was maintained at 110° C. for 10.5 hr. The excess phosphorous acid trimethyl ester was distilled-off, leaving the desired product in a purity of 89% (by $^1H$ and $^{31}P$ nmr spectra).

EXAMPLE 3

Preparation of Methacrylamidomethylphosphonic Acid 2.3 mol methacrylamidomethylphosphonic acid dimethyl ester (90%), 5.6 mol water, 8.8 g 32% hydrochloric acid, and 0.5 g hydroquinone monomethyl ether were heated for 2 hr at 70° C. in a three-neck round-bottom flask equipped with a reflux condenser, a compressed air inlet, a thermometer, a distillation head, and a mechanical stirrer. The methanol liberated in the reaction was distilled-off over 2 hr using a 70° C. bath and a water aspirator.

The desired product was obtained in a purity of 92% (by $^1H$ and $^{31}P$ nmr spectra). The yield was 434 g (97% of theoretical).

Obviously, numerous modifications and variations of the present invention are possible in light of the above teaches. It is therefore to be understood that within the scope of the appended claims, the invention may be practiced otherwise than as specifically described herein.

What is claimed as new and desired to be secured by Letters Patent of the United States is:

1. A process for preparing a (meth)acrylamidomethylphosphonic acid diester of formula I:

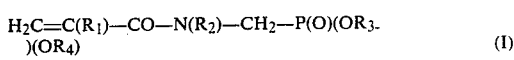

where:
$R_1$ is a hydrogen atom or a methyl group;
$R_2$ is a hydrogen atom, an unsubstituted $C_1$–$C_4$ alkyl group, a substituted $C_1$–$C_4$ alkyl group, or a $C_3$–$C_4$ alkenyl group; and
$R_3$ and $R_4$ are each independently a phenyl group, an unsubstituted $C_1$–$C_4$ alkyl group, a substituted $C_1$–$C_4$ alkyl group, or $R_3$ and $R_4$ together form an alkylene group which forms a 5- to 7-membered ring with the oxygen atoms and the phosphorous atom; said process comprising reacting, in the presence of a catalytic amount of a Lewis acid, a methylamide derivative of (meth)acrylic acid of formula II:

where X is a $C_1$–$C_{10}$ alkoxy group or a $C_2$–$C_{10}$ alkenyloxy group, with a phosphorous acid triester of formula III:

where $R_3$, $R_4$ and $R_5$ are each independently a phenyl group, an unsubstituted $C_1$–$C_4$ alkyl group, a substituted $C_1$–$C_4$ alkyl group, or $R_3$ and $R_4$ together form an alkylene group which forms a 5- to 7-membered ring with the oxygen atoms and the phosphorus atom.

2. The process of claim 1, wherein a polymerization inhibitor is used in the reaction.

3. The process of claim 2, wherein said polymerization inhibitor is hydroquinone monomethyl ether.

4. The process of claim 1, comprising using as the said Lewis acid a Friedel-Crafts catalyst.

5. The process of claim 1, comprising using as the said Lewis acid a metal compound having an organic ligand.

6. The process of claim 5, comprising using as the said metal compound having an organic ligand a compound of titanium, zirconium, hafnium, tin, zinc, aluminum, or vanadium, having as an organic ligand an alkoxy group, an aryloxy group, an acyloxy group, an alkyl group, or aryl group, wherein each group has 1 to 10 C atoms.

7. The process of claim 6, comprising using an individual metal compound or a mixture of at least two different metal compounds as the said catalyst.

8. The process of claim 7, comprising using the said catalyst in an amount of 0.01 to 10 mol.% relative to the amount of phosphonic acid ester to be produced.

9. The process of claim 8, comprising 0.1 to 5 mol.% of the said catalyst.

10. The process of claim 1, comprising running the reaction in the presence of a solvent comprising dichloromethane, 1,2-dichloroethane, tetrachloroethane, a chlorofluoro hydrocarbon, or nitrobenzene.

11. The process of claim 1, comprising using N-(methoxymethyl)-(meth)acrylamide, N-(isobutoxymethyl)-(meth)acrylamide, N-(methoxymethyl)-N-methyl-methacrylamide, N-(isobutoxymethyl)-N-methyl-methacrylamide, N-(methoxymethyl)-N-ethyl-acrylamide, N-(allyloxymethyl)-methacrylamide, or N-(cyclohexyloxymethyl)-methacrylamide.

12. The process of claim 11, comprising using N-(methoxymethyl)-(meth)acrylamide, or N-(isobutoxymethyl)-(meth)acrylamide.

13. The process of claim 1, comprising using a triphenyl ester of phosphorus acid.

14. The process of claim 1, comprising using a trimethyl ester, a triethyl ester, a triisopropyl ester, a tri-n-butyl ester, a tri-(2-chloroethyl) ester, a tri-(2-bromomethyl) ester, a 2-methoxy-1,3-dioxaphospholane, or a 2-methoxy-4-methyl-1,3-thioxaphospholane ester of phosphorus acid.

15. A composition obtained by:
(i) reacting, in the presence of a Lewis acid, a methyl amide derivative of (meth)acrylic acid of formula II:

$$H_2C=C(R_1)-CO-N(R_2)-CH_2-X \qquad (II)$$

where $R_1$ is a hydrogen atom or a methyl group, $R_2$ is a hydrogen atom, an unsubstituted $C_1-C_4$ alkyl group, a substituted $C_1-C_4$ alkyl group, or a $C_3-C_4$ alkenyl group, and X is a $C_1-C_{10}$ alkoxy group or a $C_2-C_{10}$ alkenyloxy group, with a phosphorus acid triester of formula III:

$$P(OR_3)(OR_4)(OR_5) \qquad (III)$$

where $R_3$, $R_4$ and $R_5$ are each independently a phenyl group, an unsubstituted $C_1-C_4$ alkyl group, a substituted $C_1-C_4$ alkyl group, or $R_3$ and $R_4$ together form an alkylene group which forms a 5- to 7-membered ring with the oxygen atoms and the phosphorus atom; and (ii) removing by distillation, at the end of the reaction, volatile substances in the reaction mixture.

16. The composition of claim 15, obtained by using N-(methoxymethyl)-(meth)acrylamide, N-(ethoxymethyl)-methacrylamide, N-(isobutoxymethyl)-(meth)acrylamide, N-(methoxymethyl)-N-methyl-methacrylamide, N-(isobutoxymethyl)-N-methyl-methacrylamide, N-(ethoxymethyl)-N-ethyl-acrylamide, N-(allyloxymethyl)-methacrylamide, or N-(cyclohexyloxymethyl)-methacrylamide.

17. The composition of claim 15, obtained by using N-(methoxymethyl)-(meth)acrylamide, N-(ethoxymethyl)-(meth)acrylamide, or N-(isobutoxymethyl)-(meth)acrylamide.

18. The composition of claim 15, obtained by using a triphenyl ester, a trimethyl ester, a triethyl ester, a triisopropyl ester, a tri-n-butyl ester, a tri-(2-chloroethyl) ester, a tri-(2-bromomethyl) ester, a 2-methoxy-1,3-dioxaphospholane, or a 2-ethoxy-4-methyl-1,3-dioxaphospholane.

19. The composition of claim 15, obtained by using as the said Lewis acid a Friedel-Crafts catalyst.

20. The composition of claim 15, obtained by using as the said Lewis acid a metal compound having an organic ligand.

21. The composition of claim 15, wherein step (i) is carried out in the presence of a polymerization inhibitor.

22. The composition of claim 21, wherein said polymerization inhibitor is hydroquinone monomethyl ether.

* * * * *